United States Patent
Wang et al.

(10) Patent No.: US 11,636,695 B2
(45) Date of Patent: Apr. 25, 2023

(54) METHOD FOR SYNTHESIZING IMAGE BASED ON CONDITIONAL GENERATIVE ADVERSARIAL NETWORK AND RELATED DEVICE

(71) Applicant: PING AN TECHNOLOGY(SHENZHEN)CO., LTD., Shenzhen (CN)

(72) Inventors: Yiwen Wang, Shenzhen (CN); Jianzong Wang, Shenzhen (CN)

(73) Assignee: Ping An Technology (Shenzhen) Co., Ltd., Shenzhen (CN)

(*) Notice: Subject to any disclaimer, the term of this patent is extended or adjusted under 35 U.S.C. 154(b) by 202 days.

(21) Appl. No.: 17/264,312

(22) PCT Filed: Nov. 13, 2019

(86) PCT No.: PCT/CN2019/117988
§ 371 (c)(1),
(2) Date: Jan. 29, 2021

(87) PCT Pub. No.: WO2021/027152
PCT Pub. Date: Feb. 18, 2021

(65) Prior Publication Data
US 2021/0312243 A1    Oct. 7, 2021

(30) Foreign Application Priority Data
Aug. 12, 2019   (CN) .......................... 201910741020.7

(51) Int. Cl.
*G06K 9/62* (2022.01)
*G06K 9/00* (2022.01)
(Continued)

(52) U.S. Cl.
CPC ........ *G06V 20/695* (2022.01); *G06F 18/2132* (2023.01); *G06F 18/2137* (2023.01);
(Continued)

(58) Field of Classification Search
CPC .. G06K 9/6265; G06K 9/6223; G06K 9/6234; G06K 9/6251; G06K 9/6257;
(Continued)

(56) References Cited

U.S. PATENT DOCUMENTS

2019/0244681 A1    8/2019   Gurcan et al.

FOREIGN PATENT DOCUMENTS

| CN | 107492084 A | 12/2017 |
|---|---|---|
| CN | 108388925 A | 8/2018 |

(Continued)

OTHER PUBLICATIONS

Bailo et al, "Red blood cell image generation for data augmentation using Conditional Generative Adversarial Networks", Jun. 2019, IEEE/CVF Conference on Computer Vision and Pattern Recognition Workshops (CVPRW), pp. 1039-1048 (10 pages) (Year: 2019).*

(Continued)

*Primary Examiner* — David F Dunphy
(74) *Attorney, Agent, or Firm* — ScienBiziP, P.C.

(57) ABSTRACT

A method includes: obtaining a plurality of clinical red blood cell images, dividing red blood cells of different shapes at different positions in each of the red blood cell images into a plurality of submasks, and synthesizing the submasks corresponding to each of the red blood cell images to generate one mask to obtain a plurality of masks corresponding to the red blood cell images; collecting shape data of a plurality of red blood cells from the masks to obtain a training data set, calculating a segmentation boundary of each red blood cell in the training data set, and establishing a red blood cell shape data set based on the segmentation boundary of each red blood cell; collecting distribution data of each red blood cell in the red blood cell shape data set; and synthesizing the red blood cell shape data set into a plurality of red blood cell images.

17 Claims, 2 Drawing Sheets

(51) Int. Cl.
  G06K 9/46      (2006.01)
  G06T 7/12      (2017.01)
  G06T 7/194     (2017.01)
  G16H 30/40     (2018.01)
  G16H 10/40     (2018.01)
  G06V 20/69     (2022.01)
  G06F 18/21     (2023.01)
  G06F 18/2132   (2023.01)
  G06F 18/2137   (2023.01)
  G06F 18/214    (2023.01)
  G06F 18/23213  (2023.01)
  G06V 10/762    (2022.01)
  G06V 10/764    (2022.01)
  G06V 10/82     (2022.01)

(52) U.S. Cl.
  CPC ...... *G06F 18/2148* (2023.01); *G06F 18/2193* (2023.01); *G06F 18/23213* (2023.01); *G06T 7/12* (2017.01); *G06T 7/194* (2017.01); *G06V 10/763* (2022.01); *G06V 10/764* (2022.01); *G06V 10/82* (2022.01); *G16H 10/40* (2018.01); *G16H 30/40* (2018.01); *G06T 2207/20084* (2013.01); *G06T 2207/30024* (2013.01)

(58) Field of Classification Search
  CPC . G06T 7/12; G06T 7/194; G06T 2207/20084; G06T 2207/30024; G16H 10/40; G16H 30/40; G06V 20/695; G06V 10/457; G06V 10/751
  See application file for complete search history.

(56) References Cited

FOREIGN PATENT DOCUMENTS

CN   109493330 A   3/2019
CN   109843176 A   6/2019

OTHER PUBLICATIONS

Chengcheng Li, et al., Fast-Converging Conditional Generative Adversarial Networks for Image Synthesis, ICIP 2018 IEEE, 2018, pp. 2132-2136.

* cited by examiner

METHOD FOR SYNTHESIZING IMAGE BASED ON CONDITIONAL GENERATIVE ADVERSARIAL NETWORK AND RELATED DEVICE

CROSS REFERENCE TO THE RELATED APPLICATIONS

This application is the national stage entry of International Application No. PCT/CN2019/117988, filed on Nov. 13, 2019, which is based upon and claims priority to Chinese Patent Application No. 201910741020.7, filed on Aug. 12, 2019, the entire contents of which are incorporated herein by reference.

TECHNICAL FIELD

This application relates to the neural network field, and in particular, to a method for synthesizing an image based on a conditional generative adversarial network and a related device.

BACKGROUND

In the medical field, it is necessary to collect a large amount of clinical data, mark the clinical data separately, and perform deep learning on the marked clinical data. Since marking data requires professional medical knowledge, the requirements for the marking operation are high. The inventor realizes that if clinical data is to be used and shared, it needs to be authorized by a plurality of parties such as patients, doctors, and hospitals, which is difficult to implement. In addition, before deep learning is performed on the clinical data, it is further necessary to perform compatible processing and data conversion on clinical data of different medical institutions. The operation is cumbersome and time-consuming.

SUMMARY

This application provides a method for synthesizing an image based on a conditional generative adversarial network and a related device, so as to solve the prior-art problem that processing of clinical data of different medical institutions is cumbersome.

According to a first aspect, this application provides a method for synthesizing an image based on a conditional generative adversarial network. The method includes:

obtaining a plurality of clinical red blood cell images, dividing red blood cells of different shapes at different positions in each of the red blood cell images into a plurality of submasks, and synthesizing the plurality of submasks corresponding to each of the red blood cell images to generate one mask, so as to obtain a plurality of masks corresponding to the plurality of red blood cell images, where each of the red blood cell images includes a plurality of red blood cells, and shapes and positions of the red blood cells on the same red blood cell image may be the same or different;

collecting shape data of a plurality of red blood cells from the plurality of masks to obtain a training data set, calculating a segmentation boundary of each red blood cell in the training data set, and establishing a red blood cell shape data set based on the segmentation boundary of each red blood cell, where the red blood cell shape data set is used to provide shape data of red blood cells during synthesis of a red blood cell image;

collecting distribution data of each red blood cell in the red blood cell shape data set; and synthesizing the red blood cell shape data set into a plurality of red blood cell images.

According to a second aspect, this application provides an apparatus for synthesizing an image, where the apparatus has a function of implementing the method for synthesizing an image based on a conditional generative adversarial network provided in the first aspect. The function may be implemented by hardware, or may be implemented by hardware executing corresponding software. The hardware or the software includes one or more modules corresponding to the function, and the module may be software and/or hardware.

In a possible design, the apparatus includes:

an input/output module, configured to obtain a plurality of clinical red blood cell images, divide red blood cells of different shapes at different positions in each of the red blood cell images into a plurality of submasks, and synthesize the plurality of submasks corresponding to each of the red blood cell images to generate one mask, so as to obtain a plurality of masks corresponding to the plurality of red blood cell images, where each of the red blood cell images includes a plurality of red blood cells, and shapes and positions of the red blood cells on the same red blood cell image may be the same or different; and a processing module, configured to collect shape data of a plurality of red blood cells from the plurality of masks by using the input/output module to obtain a training data set, calculate a segmentation boundary of each red blood cell in the training data set, and establish a red blood cell shape data set based on the segmentation boundary of each red blood cell, where the red blood cell shape data set is used to provide shape data of red blood cells during synthesis of a red blood cell image; collect distribution data of each red blood cell in the red blood cell shape data set by using the input/output module; and synthesize the red blood cell shape data set into a plurality of red blood cell images.

A third aspect of this application provides a computer device, where the computer device includes at least one connected processor, a memory, and a transceiver, the memory is configured to store program code, and the processor is configured to invoke the program code in the memory to perform the method according to the first aspect.

A fourth aspect of this application provides a computer storage medium, where the storage medium stores a computer instruction, and when the computer instruction runs on a computer, the computer is enabled to perform the method according to the first aspect.

Compared with the prior art, in the solution provided in this application, a plurality of clinical red blood cell images are obtained, red blood cells of different shapes at different positions in each of the red blood cell images are divided into a plurality of submasks, and the plurality of submasks corresponding to each of the red blood cell images are synthesized to generate one mask, so as to obtain a plurality of masks corresponding to the plurality of red blood cell images; shape data of a plurality of red blood cells is collected from the plurality of masks to obtain a training data set, a segmentation boundary of each red blood cell in the training data set is calculated, and a red blood cell shape data set is established based on the segmentation boundary of each red blood cell; distribution data of each red blood cell in the red blood cell shape data set is collected; and the red blood cell shape data set is synthesized into a plurality of red blood cell images. In this solution, existing clinical data can be simulated and augmented when a large amount of real clinical data is lacking.

DETAILED DESCRIPTION OF THE EMBODIMENTS

It should be understood that the specific embodiments described herein are merely used to explain this application but are not intended to limit this application. In the specification, claims, and accompanying drawings of this application, the terms "first", "second", and the like are intended to distinguish between similar objects but do not necessarily indicate a specific order or sequence. It should be understood that the terms used in such a way are interchangeable in proper circumstances so that the embodiments of this application described herein can be implemented in other orders than the order illustrated or described herein. In addition, the terms "include", "have", or any other variant thereof are intended to cover a non-exclusive inclusion. For example, a process, a method, a system, a product, or a device that includes a series of steps or modules is not necessarily limited to the steps or modules that are expressly listed, but may include another step or module not expressly listed or inherent to the process, the method, the product, or the device. The module division in this application is merely logical division, and there may be another division during implementation in actual application. For example, a plurality of modules may be combined or integrated into another system, or some features may be ignored or not performed.

This application provides a method for synthesizing an image based on a conditional generative adversarial network, and a related device, which can be applied to a feature encoder network.

To solve the foregoing technical problem, this application mainly provides the following technical solutions:

A new red blood cell image is synthesized based on a conditional generative adversarial nets (CGAN) algorithm, achieving data augmentation to meet deep learning needs. To synthesize a new red blood cell image, a mask needs to be first generated through synthesis, and the generated mask is then converted into a realistic image.

Figure 1:
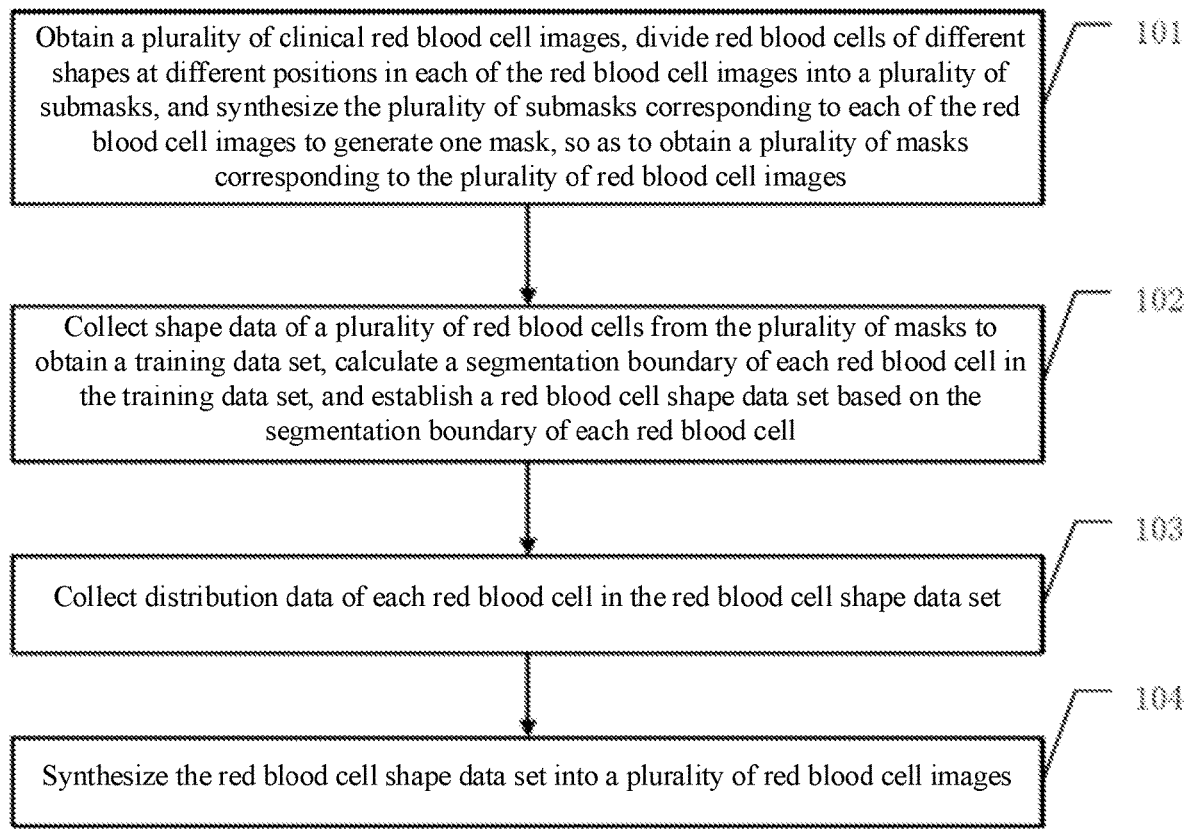
FIG. 1 is a schematic flowchart of a method for synthesizing an image based on a conditional generative adversarial network according to an embodiment of this application.

Referring to FIG. 1, the following describes a method for synthesizing an image based on a conditional generative adversarial network according to an embodiment of this application. The method includes:

101. Obtain a plurality of clinical red blood cell images, divide red blood cells of different shapes at different positions in each of the red blood cell images into a plurality of submasks, and synthesize the plurality of submasks corresponding to each of the red blood cell images to generate one mask, so as to obtain a plurality of masks corresponding to the plurality of red blood cell images.

Each of the red blood cell images includes a plurality of red blood cells, and shapes and positions of the red blood cells on the same red blood cell image may be the same or different.

In some implementations, the synthesizing the plurality of submasks corresponding to each of the red blood cell images to generate one mask, so as to obtain a plurality of masks corresponding to the plurality of red blood cell images includes:

invoking a red blood cell shape sampler to iteratively select a red blood cell shape $s_i$ from the red blood cell shape data set, where $1 \leq i \leq n$ and i is a positive integer; and placing the selected red blood cell shape s in the submasks to obtain the mask.

Specifically, the red blood cells of different shapes at different positions are used to generate a synthesized instance segmentation mask, that is, the mask. To be specific, the shape of the red blood cell and the position of the red blood cell in the red blood cell image are obtained, and an expression of the mask obtained after synthesis is as follows:

$$(\{(s_1,l_1),s_2,l_2), \ldots ,(s_n,l_n), \text{background}\} \quad (1)$$

where, $s_1, s_2, \ldots,$ and $s_n$ all represent the shapes of red blood cells, $l_n$ represents the positions of red blood cells in a red blood cell image, $(s_n,l_n)$ represents a submask, n represents the total number of red blood cells in a red blood cell image, n is a positive integer, and background represents a background pixel image of the red blood cell image.

The shapes of red blood cells, the total number of red blood cells in a red blood cell image, and the positions of red blood cells in a red blood cell image are normally distributed, and an expression of the normal distribution is n~Norm $(\mu_n, \sigma_n)$, where $\mu_n$ and $\sigma_n$ are determined by the training set.

Optionally, when $s_i$ is selected, a probability density function can be used to select $s_i$. The probability density function can be used to calculate a set of probabilities. The set of probabilities is used to enhance appearance features of red blood cell shapes $s_i$, for example, enriching the appearance of red blood cells, including rotation, zooming, horizontal/vertical flipping, etc.

102. Collect shape data of a plurality of red blood cells from the plurality of masks to obtain a training data set, calculate a segmentation boundary of each red blood cell in the training data set, and establish a red blood cell shape data set based on the segmentation boundary of each red blood cell.

The red blood cell shape data set is used to provide shape data of red blood cells during synthesis of a red blood cell image.

In some implementations, the collecting shape data of a plurality of red blood cells from the plurality of masks to obtain a training data set, calculating a segmentation boundary of each red blood cell in the training data set, and establishing a red blood cell shape data set based on the segmentation boundary of each red blood cell includes:

identifying a discontinuous background region in a background image through image segmentation, marking the discontinuous background region, and determining a segmentation threshold;

performing edge detection on cell membranes of red blood cells in each red blood cell image region by using an edge detection method, to obtain an 8-connected edge of a single pixel in each red blood cell image region;

comparing the segmentation threshold with a grayscale value of a pixel, performing pixel segmentation on the red blood cell image based on the segmentation threshold to obtain a plurality of red blood cell image regions, and performing grayscale stretching on the 8-connected edge of a single pixel in each red blood cell image region to segment the red blood cell image background and the grayscale value of the 8-connected edge of a single pixel to obtain a binary image;

performing a fill operation on the binary image to fill the interior of each red blood cell in the binary image; and performing canny edge detection on the filled binary image to obtain a segmentation boundary (which may also be referred to as a contour) of each red blood cell.

When grayscale stretching is performed on the 8-connected edge of a single pixel in each red blood cell image region, the following conversion formula is used to segment the red blood cell image background and the grayscale value of the 8-connected edge of a single pixel to obtain the binary image:

$$g(i, j) = \begin{cases} 1, & f(i, j) \geq T \\ 0, & f(i, j) < T \end{cases}$$

where, T represents the segmentation threshold, f(i,j) represents an input red blood cell image, and g(i,j) represents an output red blood cell image. When the red blood cell image is segmented, for the pixels in the red blood cell region, g(i,j)=1, and for the pixels in the background region, g(i,j)=0.

Optionally, the segmentation boundaries of all red blood cells can also be extracted for size judging. If the segmentation boundary is less than a preset threshold, it is considered that a red blood cell whose segmentation boundary is less than the preset threshold is not a red blood cell.

It can be learned from the foregoing description that filling the interiors of the red blood cells in the middle can avoid double edges of the red blood cells inside; filling the interior of each red blood cell in the binary image can avoid double edges of the red blood cells inside.

103. Collect distribution data of each red blood cell in the red blood cell shape data set.

In some implementations, an estimation of distribution algorithm may be used to separately collect a position of each red blood cell in a canvas in a probability density function in two-dimensional discrete space.

Specifically, the collecting distribution data of each red blood cell in the red blood cell shape data set includes:

using the estimation of distribution algorithm to locate the position of each red blood cell in the red blood cell shape data set and the position of each pixel in each red blood cell;

separately calculating, based on the probability density function, the position of each red blood cell and the position of each pixel, a prior probability of each pixel being selected as a red blood cell center;

generating a possibility image set P(i) corresponding to each red blood cell from the prior probability of each pixel being selected as a red blood cell center and each red blood cell;

sequentially selecting a prior probability from the possibility image set P(i) based on the value of i in ascending order, and simulating a real adhesion state of red blood cells for each value of i; and calculating the distribution data of each red blood cell in the red blood cell shape data set based on the position of each red blood cell and the position of each pixel in the real adhesion state of red blood cells simulated for each value of i.

Optionally, the probability density function is represented by a possibility image set P(i), and a formula for collecting a position $1_i$ of an i-th red blood cell from the possibility image set P(i) is as follows:

$$l_i \sim P(i) \quad (2)$$

where, the value of each pixel in P(i) refers to a prior probability of the pixel being selected as the red blood cell center in an i-th step. When the first $n_{init}$ cell is extracted, P(i) is initially uniform. When i increases, P(i) changes the shape. Positions $l_i$ of red blood cells of different shapes are extracted from P(i) at a time by using formula (2) based on the value of i in descending order. Therefore, the entire process of extracting red blood cells from P(i) can simulate the real adhesion state of red blood cells. In some implementations, the Markov stochastic process can be used to simulate natural evolution of P(i). An expression is as follows:

$$\mathcal{P}(i) = \begin{cases} \text{uniform}, & i \leq n_{init} \\ (1 - a_i)\mathcal{P}(i-1) + a_i z(l_{i-1}), & i > n_{init} \end{cases} \quad (3)$$

An excitation function $z(l_i)$ surrounds a collected cell center $l_i$ and is calculated according to a two-dimensional Gaussian function ($\sigma = \sigma x = \sigma y$). A purpose of this step is to reduce the possibility of boundaries of red blood cells that have been allocated, so as to prevent red blood cells from overlapping. An amount of increments depends on a standard coefficient $a_i$ (ai=1/i). At any time point, the sum of P(i) is 1.

In fact, when red blood cells are located in the synthesized mask, the red blood cells are always on the canvas of the synthesized mask at any time. Therefore, a color can be given to make the red blood cells in contact have different colors. If this condition cannot be met, the coordinate collection process is repeated. Since the colors of red blood cells in contact are different, the generated synthesized mask can be used as an instance segmentation mask with the possibility of extracting each red blood cell.

104. Synthesize the red blood cell shape data set into a plurality of red blood cell images.

In this application, a generator G for generating red blood cell images and two multi-scale discriminators (referred to as D1 and D2 for short) are provided in a feature encoder network E.

In some implementations, the synthesizing the red blood cell shape data set into a plurality of red blood cell images includes:

inputting the red blood cell shape data set into the generator G;

the generator G converts the segmentation mask in the red blood cell shape data set into a plurality of red blood cell images, and inputs the plurality of red blood cell images obtained through the conversion into the two multi-scale discriminators D, where the plurality of red blood cell images obtained through the conversion are all images that simulate realistic red blood cells;

the two multi-scale discriminators D perform discrimination at least once between the real red blood cell image and the synthesized red blood cell image within a preset period of time, so as to train a neural network model;

the two multi-scale discriminators D output training results;

a feature encoder network E combines the training results with the red blood cell shape data set x to obtain a combined result, where the combined result is used to control the style of synthesizing the red blood cell image;

inputting the plurality of masks into the generator at the stage of synthesizing the red blood cell image; and the generator synthesizes the plurality of masks into the red blood cell image; where the combined result can be obtained by using a K-means clustering algorithm to generate a plurality of clusters, such as 10 clusters, from the training results and the red blood cell shape data set. The style of the red blood cell image obtained through the synthesis is determined by the encoder E based on randomly collected features of the plurality of clusters.

In some implementations, a complete network training target is as follows:

$$\min_G \left( \left( \max_{D_1, D_2} \sum_{k=1,2} L_{GAN}(G, D_k) \right) + \lambda_{FM} \sum_{k=1,2} L_{FM}(G, D_k) + \lambda_{PR} L_{PR}(G(x, E(x)), y) \right)$$

where, x represents the red blood cell shape data set, LGAN(G, Dk) represents an adversarial loss, and an expression of the adversarial loss is as follows:

$$E_{(x,y)}[\log D_k(x,y)] + E_x[\log(1 - D_k(x, G(x, E(x))))]$$

LFM(G; Dk) represents a feature matching loss, and the feature matching loss is used to stabilize the training results and produce better visual results on a plurality of scales. An expression of the feature matching loss is as follows:

$$E_{(x,y)} \sum_{i=1}^{T} \frac{1}{N_i} [\|D_k^{(i)}(x, y) - D_k^{(i)}(x, G(x, E(x)))\|_1]$$

LPR(G(x); y) represents a perceptual reconstruction loss, and the perceptual reconstruction loss is used to further improve quality of a synthesized image. An expression of the perceptual reconstruction loss is as follows:

$$\sum_{i=1}^{N} \frac{1}{M_i} [\|F^{(i)}(y) - F^{(i)}(x, G(x, E(x)))\|_1]$$

Compared with the existing mechanism, in the embodiments of this application, when a large amount of real clinical data is lacking, data simulation and augmentation of existing clinical data can also be performed to generate realistic clinical data, and then deep learning is performed based on the simulated and augmented clinical data, thereby breaking the format compatibility limitations of different data sources and meeting the needs of deep learning.

Figure 2:
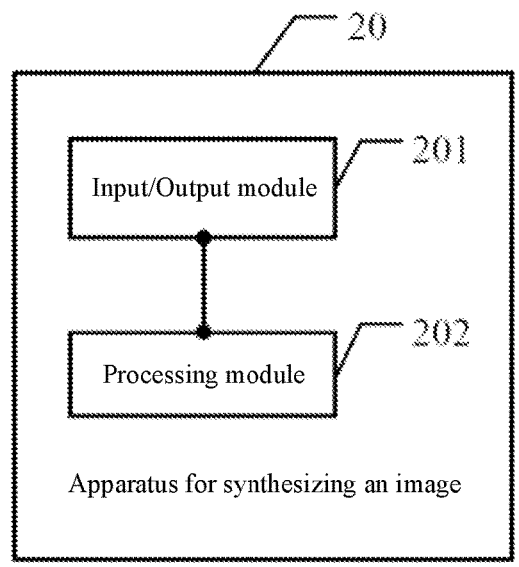
FIG. 2 is a schematic structural diagram of an apparatus 20 for synthesizing an image according to an embodiment of this application.
Figure 3:
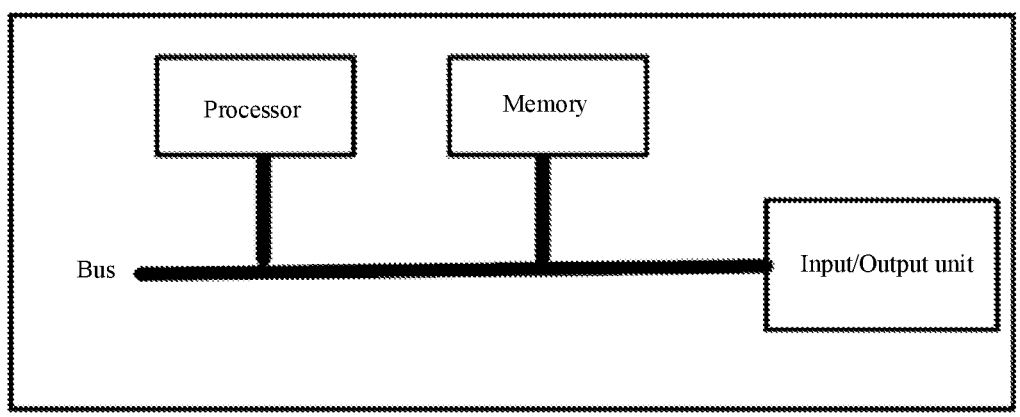
FIG. 3 is a schematic structural diagram of a computer device according to an embodiment of this application.

The technical features mentioned in the embodiment or implementation corresponding to FIG. 1 are also applicable to embodiments corresponding to FIG. 2 and FIG. 3 in this application. Similar content is not described below.

The foregoing describes the method for synthesizing an image based on a conditional generative adversarial network in this application. The following describes an apparatus for performing the method for synthesizing an image based on a conditional generative adversarial network.

FIG. 2 is a schematic structural diagram of an apparatus 20 for synthesizing an image. The apparatus 20 can be used to recognize a red blood cell image. The apparatus 20 in an embodiment of this application can implement the steps corresponding to the method for synthesizing an image based on a conditional generative adversarial network performed in the embodiment corresponding to FIG. 1. The function implemented by the apparatus 20 may be implemented by hardware, or may be implemented by hardware by executing corresponding software. The hardware or the software includes one or more modules corresponding to the function, and the module may be software and/or hardware. The apparatus 20 may include an input/output module 201 and a processing module 202. For implementation of functions of the processing module 202 and the input/output module 201, reference can be made to the operations performed in the embodiment corresponding to FIG. 1, and details are not described herein. The processing module 202 can be configured to control input/output or receiving and sending operations of the input/output module 201.

In some implementations, the input/output module 201 can be configured to obtain a plurality of clinical red blood cell images, divide red blood cells of different shapes at different positions in each of the red blood cell images into a plurality of submasks, and synthesize the plurality of submasks corresponding to each of the red blood cell images to generate one mask, so as to obtain a plurality of masks corresponding to the plurality of red blood cell images, where each of the red blood cell images includes a plurality of red blood cells, and shapes and positions of the red blood cells on the same red blood cell image may be the same or different; and the processing module 202 can be configured to collect shape data of a plurality of red blood cells from the plurality of masks by using the input/output module to obtain a training data set, calculate a segmentation boundary of each red blood cell in the training data set, and establish a red blood cell shape data set based on the segmentation boundary of each red blood cell, where the red blood cell shape data set is used to provide shape data of red blood cells during synthesis of a red blood cell image; collect distribution data of each red blood cell in the red blood cell shape data set by using the input/output module; and synthesize the red blood cell shape data set into a plurality of red blood cell images.

In some implementations, the processing module is specifically configured to:

invoke a red blood cell shape sampler to iteratively select a red blood cell shape $s_i$ from the red blood cell shape data set, where $1 \le i \le n$ and i is a positive integer, and $s_i$ represents red blood cells of different shapes at different positions; and place the selected red blood cell shape $s_i$ in the submasks to obtain the red blood cell shape and the position of the red blood cell in the red blood cell image, and use the obtained red blood cell shape and the obtained position of the red blood cell in the red blood cell image as the mask; where an expression of the mask is as follows:

$$\{(s_1, l_1), (s_2, l_2), \ldots, (s_n, l_n), \text{background}\}$$

where, $s_1, s_2, \ldots,$ and $s_n$ all represent the shapes of red blood cells, $l_n$ represents the positions of red blood cells in a red blood cell image, $(s_n, l_n)$ represents a submask, n represents the total number of red blood cells in a red blood cell image, n is a positive integer, and background represents a background pixel image of the red blood cell image.

In some implementations, the processing module is specifically configured to:

identify a discontinuous background region in a background image through image segmentation, mark the discontinuous background region, and determine a segmentation threshold;

perform edge detection on cell membranes of red blood cells in each red blood cell image region by using an edge detection method, to obtain an 8-connected edge of a single pixel in each red blood cell image region;

compare the segmentation threshold with a grayscale value of a pixel, perform pixel segmentation on the red blood cell image based on the segmentation threshold to obtain a plurality of red blood cell image regions, and perform grayscale stretching on the 8-connected edge of a single pixel in each red blood cell image region to segment the red blood cell image background and the grayscale value of the 8-connected edge of a single pixel to obtain a binary image;

perform a fill operation on the binary image to fill the interior of each red blood cell in the binary image; and perform canny edge detection on the filled binary image to obtain a segmentation boundary of each red blood cell; where when grayscale stretching is performed on the 8-connected edge of a single pixel in each red blood cell image region, the following conversion formula is used to segment the red blood cell image background and the grayscale value of the 8-connected edge of a single pixel to obtain the binary image g(i,j):

$$g(i, j) = \begin{cases} 1, f(i, j) \geq T \\ 0, f(i, j) < T \end{cases}$$

where, T represents the segmentation threshold, f(i,j) represents an input red blood cell image, and g(i,j) represents an output red blood cell image.

In some implementations, the processing module is specifically configured to:

use an estimation of distribution algorithm to locate the position of each red blood cell in the red blood cell shape data set and the position of each pixel in each red blood cell;

separately calculate, based on the probability density function, the position of each red blood cell and the position of each pixel, a prior probability of each pixel being selected as a red blood cell center;

generate a possibility image set P(i) corresponding to each red blood cell from the prior probability of each pixel being selected as a red blood cell center and each red blood cell;

sequentially select a prior probability from the possibility image set P(i) based on the value of i in ascending order, and simulate a real adhesion state of red blood cells for each value of i; and calculate the distribution data of each red blood cell in the red blood cell shape data set based on the position of each red blood cell and the position of each pixel in the real adhesion state of red blood cells simulated for each value of i.

In some implementations, the processing module is specifically configured to:

input the red blood cell shape data set into a generator G;

convert, by the generator G, the segmentation mask in the red blood cell shape data set into a plurality of red blood cell images, and input the plurality of red blood cell images obtained through the conversion into two multi-scale discriminators D, where the plurality of red blood cell images obtained through the conversion are all images that simulate realistic red blood cells;

perform, by the two multi-scale discriminators D, discrimination at least once between the real red blood cell image and the synthesized red blood cell image within a preset period of time, so as to train a neural network model;

output, by the two multi-scale discriminators D, training results;

combine, by a feature encoder network E, the training results with the red blood cell shape data set x to obtain a combined result, where the combined result is used to control a style of synthesizing the red blood cell image; the combined result can be obtained by using a K-means clustering algorithm to generate a plurality of clusters from the training results and the red blood cell shape data set; the style of the red blood cell image obtained through the synthesis is determined by the encoder E based on randomly collected features of the plurality of clusters;

input the plurality of masks into the generator by using the input/output module at the stage of synthesizing the red blood cell image; and synthesize, by the generator, the plurality of masks into the red blood cell image.

A physical device corresponding to the input/output module 201 shown in FIG. 2 is an input/output unit shown in FIG. 3. The input/output unit can implement some or all of functions of an acquisition module 1, or implement functions the same as or similar to those of the input/output module 201.

A physical device corresponding to the processing module 202 shown in FIG. 2 is a processor shown in FIG. 3. The processor can implement some or all of the functions of the processing module 202, or implement functions the same as or similar to those of the processing module 202.

The foregoing separately describes the apparatus 20 in the embodiment of this application from the perspective of modular functional entities. The following describes a computer device from the perspective of hardware, as shown in FIG. 3. The computer device includes: a processor, a memory, a transceiver (which may also be an input/output unit, not shown in FIG. 3), and a computer program that is stored in the memory and that can run on the processor. For example, the computer program may be a program corresponding to the method for synthesizing an image based on a conditional generative adversarial network in the embodiment corresponding to FIG. 1. For example, when the computer device implements the functions of the apparatus 20 shown in FIG. 2, the processor executes the computer program to implement the steps of the method for synthesizing an image based on a conditional generative adversarial network performed by the apparatus 20 in the embodiment corresponding to FIG. 2; or the processor executes the computer program to implement the functions of various modules in the apparatus 20 in the embodiment corresponding to FIG. 2. For another example, the computer program may be a program corresponding to the method for synthesizing an image based on a conditional generative adversarial network in the embodiment corresponding to FIG. 1.

This application further provides a computer-readable storage medium. The computer-readable storage medium may be a non-volatile computer-readable storage medium, or may be a non-transitory storage medium. The computer-readable storage medium stores a computer instruction, and when the computer instruction runs on a computer, the computer is enabled to perform the following steps:

obtaining a plurality of clinical red blood cell images, dividing red blood cells of different shapes at different positions in each of the red blood cell images into a plurality of submasks, and synthesizing the plurality of submasks corresponding to each of the red blood cell images to generate one mask, so as to obtain a plurality of masks corresponding to the plurality of red blood cell images, where each of the red blood cell images includes a plurality of red blood cells, and shapes and positions of the red blood cells on the same red blood cell image may be the same or different;

collecting shape data of a plurality of red blood cells from the plurality of masks to obtain a training data set, calculating a segmentation boundary of each red blood cell in the training data set, and establishing a red blood cell shape data set based on the segmentation boundary of each red blood cell, where the red blood cell shape data set is used to provide shape data of red blood cells during synthesis of a red blood cell image;

collecting distribution data of each red blood cell in the red blood cell shape data set; and synthesizing the red blood cell shape data set into a plurality of red blood cell images.

From the foregoing descriptions of the implementations, a person skilled in the art can clearly understand that the method in the embodiments may be implemented by software and a necessary universal hardware platform, and certainly may alternatively be implemented by hardware. However, in many cases, the implementation performed by software and a necessary universal hardware platform is better. Based on such an understanding, the technical solutions of this application essentially or the part contributing to the prior art may be implemented in a form of a software product. The computer software product is stored in a storage medium (for example, a ROM/RAM), and includes several instructions for instructing a terminal (which may be a mobile phone, a computer, a server, a network device, or the like) to perform the methods described in the embodiments of this application.

The embodiments of this application are described with reference to the accompanying drawings above. However, this application is not limited to the foregoing specific implementations, which are merely examples but not limitations. A person of ordinary skill in the art may make many forms under the teaching of this application without departing from the purpose of this application and the protection scope of the claims. All of equivalent structures or equivalent process variations made by using the specification and the accompanying drawings of this application, or those directly or indirectly applied in other related technical fields shall fall within the protection scope of this application.

The invention claimed is:

1. A method for synthesizing an image based on a conditional generative adversarial network, comprising:

obtaining a plurality of clinical red blood cell images, dividing red blood cells of different shapes at different positions in each of the plurality of clinical red blood cell images into a plurality of submasks, and synthesizing the plurality of submasks corresponding to each of the plurality of clinical red blood cell images to generate one mask, and to obtain a plurality of masks corresponding to the plurality of red blood cell images, wherein each of the plurality of clinical red blood cell images comprises a plurality of red blood cells, and shapes and positions of the plurality of red blood cells on the same red blood cell image are identical or different;

collecting shape data of the plurality of red blood cells from the plurality of masks to obtain a training data set, calculating a segmentation boundary of each red blood cell in the training data set, and establishing a red blood cell shape data set based on the segmentation boundary of the each red blood cell, wherein the red blood cell shape data set is used to provide the shape data of the plurality of red blood cells during synthesis of a red blood cell image, wherein the step of collecting the shape data of the plurality of red blood cells from the plurality of masks to obtain the training data set, calculating the segmentation boundary of the each red blood cell in the training data set, and establishing the red blood cell shape data set based on the segmentation boundary of the each red blood cell comprises:

identifying a discontinuous background region in a background image through image segmentation, marking the discontinuous background region, and determining a segmentation threshold;

performing an edge detection on cell membranes of the plurality of red blood cells in each red blood cell image region by using an edge detection method, and obtaining an 8-connected edge of a single pixel in the each red blood cell image region;

comparing the segmentation threshold with a grayscale value of a pixel, performing a pixel segmentation on the red blood cell image based on the segmentation threshold and obtaining a plurality of red blood cell image regions, and performing a grayscale stretching on the 8-connected edge of the single pixel in the each red blood cell image region to segment a red blood cell image background and a grayscale value of the 8-connected edge of the single pixel and obtaining a binary image;

performing a fill operation on the binary image to fill an interior of the each red blood cell in the binary image and obtaining a filled binary image; and performing a canny edge detection on the filled binary image and obtaining the segmentation boundary of the each red blood cell; wherein when the grayscale stretching is performed on the 8-connected edge of the single pixel in the each red blood cell image region, segmenting the red blood cell image background and the grayscale value of the 8-connected edge of the single pixel and obtaining the binary image g(i,j) by using a conversion formula of:

$$g(i,j) = \begin{cases} 1, & f(i,j) \geq T \\ 0, & f(i,j) < T \end{cases},$$

wherein, T represents the segmentation threshold, f(i,j) represents an input red blood cell image, and g(i,j) represents an output red blood cell image;

collecting distribution data of the each red blood cell in the red blood cell shape data set; and synthesizing the red blood cell shape data set into a plurality of red blood cell images.

2. The method according to claim 1, wherein the step of synthesizing the plurality of submasks corresponding to each of the plurality of clinical red blood cell images to generate one mask, and to obtain the plurality of masks corresponding to the plurality of red blood cell images comprises:

invoking a red blood cell shape sampler to iteratively select a red blood cell shape $s_i$ from the red blood cell shape data set, wherein 1≤i≤n and i is a positive integer, and $s_i$ represents red blood cells of different shapes at different positions; and placing the selected red blood cell shape $s_i$ in the submasks to obtain the red blood cell shape and a position of the red blood cell in the red blood cell image, and using the obtained red blood cell shape and the position of the red blood cell in the red blood cell image as the mask; wherein an expression of the mask is as follows:

$$\{(s_1,l_1),(s_2,l_2),\ldots,(s_n,l_n),\text{background}\}$$

wherein, $s_1, s_2, \ldots$, and $s_n$ all represent the shapes of the plurality of red blood cells, $l_n$ represents the positions of the plurality of red blood cells in the red blood cell image, $(s_n,l_n)$ represents a submask, n represents the total number of the plurality of red blood cells in the background red blood cell image, n is a positive integer, and represents a background pixel image of the red blood cell image.

3. The method according to claim 1, wherein the step of collecting the distribution data of the each red blood cell in the red blood cell shape data set comprises:

using an estimation of distribution algorithm to locate the position of the each red blood cell in the red blood cell shape data set and a position of each pixel in the each red blood cell;

based on a probability density function, the position of the each red blood cell and the position of the each pixel, calculating a prior probability that the each pixel is selected as a red blood cell center;

generating a possibility image set P(i) corresponding to the each red blood cell from the prior probability that the each pixel is selected as the red blood cell center and the each red blood cell;

sequentially selecting the prior probability from the possibility image set P(i) based on the value of i in ascending order, and simulating a real adhesion state of red blood cells for each value of i; and calculating the distribution data of the each red blood cell in the red blood cell shape data set based on the position of the each red blood cell and the position of the each pixel in the real adhesion state of the plurality of red blood cells simulated for the each value of i.

4. The method according to claim 3, wherein the step of synthesizing the red blood cell shape data set into the plurality of red blood cell images comprises:

inputting the red blood cell shape data set into a generator G;

converting, by the generator G, the segmentation mask in the red blood cell shape data set into the plurality of red blood cell images, and inputting the plurality of red blood cell images obtained through the conversion into two multi-scale discriminators D, wherein the plurality of red blood cell images obtained through the conversion are all images that simulate realistic red blood cells;

performing, by the two multi-scale discriminators D, discrimination at least once between a real red blood cell image and a synthesized red blood cell image within a preset period of time, and to train a neural network model;

outputting, by the two multi-scale discriminators D, training results;

combining, by a feature encoder network E, the training results with the red blood cell shape data set x to obtain a combined result, wherein the combined result is used to control a style of synthesizing the red blood cell image; the combined result is obtained by using a K-means clustering algorithm to generate a plurality of clusters from the training results and the red blood cell shape data set; the style of synthesizing the red blood cell image is determined by the feature encoder network E based on randomly collected features of the plurality of clusters;

inputting the plurality of masks into the generator at a stage of synthesizing the red blood cell image; and synthesizing, by the generator, the plurality of masks into the red blood cell image.

5. The method according to claim 4, wherein a complete network training target is as follows:

$$\min_G \left( \left( \max_{D_1,D_2} \sum_{k=1,2} L_{GAN}(G, D_k) \right) + \lambda_{FM} \sum_{k=1,2} L_{FM}(G, D_k) + \lambda_{PR} L_{PR}(G(x, E(x)), y) \right),$$

wherein, x represents the red blood cell shape data set, $L_{GAN}(G,D_k)$ represents an adversarial loss, and an expression of the adversarial loss is as follows:

$$E_{(x,y)}[\log D_k(x,y)] + E_x[\log(1-D_k(x,G(x,E(x))))]$$

wherein, $L_{FM}(G,D_k)$ represents a feature matching loss, the feature matching loss is used to stabilize the training results and compensate visually generated results on a plurality of scales, and an expression of the feature matching loss is as follows:

$$E_{(x,y)} \sum_{i=1}^{T} \frac{1}{N_i} [\|D_k^{(i)}(x, y) - D_k^{(i)}(x, G(x, E(x)))\|1],$$

wherein, $L_{PR}(G(x,E(x)),y)$ represents a perceptual reconstruction loss, and an expression of the perceptual reconstruction loss is as follows:

$$\sum_{i=1}^{N} \frac{1}{M_i} [\|F^{(i)}(y) - F^{(i)}(x, G(x, E(x)))\|1].$$

6. The method according to claim 1, wherein after segmenting the red blood cell image background and the grayscale value of the 8-connected edge of the single pixel to obtain the binary image g(i,j), the method further comprises:

when the red blood cell image is segmented, for pixels in a red blood cell region, setting g(i,j)=1 and for the pixels in a background region, setting g(i,j)=0.

7. A computer device, comprising a memory, a processor, and a computer program, wherein the computer program is stored in the memory and runs on the processor, and the processor executes the computer program to perform the following steps:

obtaining a plurality of clinical red blood cell images, dividing red blood cells of different shapes at different positions in each of the plurality of clinical red blood cell images into a plurality of submasks, and synthesizing the plurality of submasks corresponding to each of the plurality of clinical red blood cell images to generate one mask, and to obtain a plurality of masks corresponding to the plurality of red blood cell images, wherein each of the plurality of clinical red blood cell images comprises a plurality of red blood cells, and shapes and positions of the plurality of red blood cells on the same red blood cell image are identical or different;

collecting shape data of the plurality of red blood cells from the plurality of masks to obtain a training data set, calculating a segmentation boundary of each red blood cell in the training data set, and establishing a red blood cell shape data set based on the segmentation boundary of the each red blood cell, wherein the red blood cell shape data set is used to provide the shape data of the plurality of red blood cells during synthesis of a red blood cell image, wherein the processor executes the computer program to collect the shape data of the plurality of red blood cells from the plurality of masks to obtain the training data set, to calculate the segmentation boundary of the each red blood cell in the training data set, and to establish the red blood cell shape data set based on the segmentation boundary of the each red blood cell, comprising the following steps:

identifying a discontinuous background region in a background image through image segmentation, marking the discontinuous background region, and determining a segmentation threshold;

performing an edge detection on cell membranes of the plurality of red blood cells in each red blood cell image region by using an edge detection method, and obtaining an 8-connected edge of a single pixel in the each red blood cell image region;

comparing the segmentation threshold with a grayscale value of a pixel, performing a pixel segmentation on the red blood cell image based on the segmentation threshold and obtaining a plurality of red blood cell image regions, and performing a grayscale stretching on the 8-connected edge of the single pixel in the each red blood cell image region to segment a red blood cell image background and a grayscale value of the 8-connected edge of the single pixel and obtaining a binary image;

performing a fill operation on the binary image to fill an interior of the each red blood cell in the binary image and obtaining a filled binary image; and performing a canny edge detection on the filled binary image and obtaining the segmentation boundary of the each red blood cell; wherein when the grayscale stretching is performed on the 8-connected edge of the single pixel in the each red blood cell image region, segmenting the red blood cell image background and the grayscale value of the 8-connected edge of the single pixel and obtaining the binary image g(i,j) by using a conversion formula of:

$$g(i, j) = \begin{cases} 1, & f(i, j) \geq T \\ 0, & f(i, j) < T \end{cases},$$

wherein, T represents the segmentation threshold, f(i,j) represents an input red blood cell image, and g(i,j) represents an output red blood cell image;

collecting distribution data of the each red blood cell in the red blood cell shape data set; and synthesizing the red blood cell shape data set into a plurality of red blood cell images.

8. The computer device according to claim 7, wherein the processor executes the computer program to synthesize the plurality of submasks corresponding to each of the plurality of clinical red blood cell images to generate one mask, and to obtain the plurality of masks corresponding to the plurality of red blood cell images, comprising the following steps:

invoking a red blood cell shape sampler to iteratively select a red blood cell shape $s_i$ from the red blood cell shape data set, wherein $1 \leq i \leq n$ and i is a positive integer, and $s_i$ represents red blood cells of different shapes at different positions; and placing the selected red blood cell shape $s_i$ in the submasks to obtain the red blood cell shape and a position of the red blood cell in the red blood cell image, and using the obtained red blood cell shape and the position of the red blood cell in the red blood cell image as the mask; wherein an expression of the mask is as follows:

$$\{(s_1,l_1),(s_2,l_2), \ldots ,(s_n,l_n),\text{background}\}$$

wherein, $s_1, s_2, \ldots$, and $s_n$ all represent the shapes of the plurality of red blood cells, $l_n$ represents the positions of the plurality of red blood cells in the red blood cell image, $(s_n,l_n)$ represents a submask, n represents the total number of the plurality of red blood cells in the background red blood cell image, n is a positive integer, and represents a background pixel image of the red blood cell image.

9. The computer device according to claim 7, wherein the processor executes the computer program to collect the distribution data of the each red blood cell in the red blood cell shape data set, comprising the following steps:

using an estimation of distribution algorithm to locate the position of the each red blood cell in the red blood cell shape data set and a position of each pixel in the each red blood cell;

based on a probability density function, the position of the each red blood cell and the position of the each pixel, calculating a prior probability that the each pixel is selected as a red blood cell center;

generating a possibility image set P(i) corresponding to the each red blood cell from the prior probability that the each pixel is being-selected as the red blood cell center and the each red blood cell;

sequentially selecting the prior probability from the possibility image set P(i) based on the value of i in ascending order, and simulating a real adhesion state of red blood cells for each value of i; and calculating the distribution data of the each red blood cell in the red blood cell shape data set based on the position of the each red blood cell and the position of the each pixel in the real adhesion state of the plurality of red blood cells simulated for the each value of i.

10. The computer device according to claim 9, wherein the processor executes the computer program to synthesize the red blood cell shape data set into the plurality of red blood cell images, comprising the following steps:

inputting the red blood cell shape data set into a generator G;

converting, by the generator G, the segmentation mask in the red blood cell shape data set into the plurality of red blood cell images, and inputting the plurality of red blood cell images obtained through the conversion into two multi-scale discriminators D, wherein the plurality of red blood cell images obtained through the conversion are all images that simulate realistic red blood cells;

performing, by the two multi-scale discriminators D, discrimination at least once between a real red blood cell image and a synthesized red blood cell image within a preset period of time, and to train a neural network model;

outputting, by the two multi-scale discriminators D, training results;

combining, by a feature encoder network E, the training results with the red blood cell shape data set x to obtain a combined result, wherein the combined result is used to control a style of synthesizing the red blood cell image; the combined result is obtained by using a K-means clustering algorithm to generate a plurality of clusters from the training results and the red blood cell shape data set; the style of synthesizing the red blood cell image is determined by the feature encoder network E based on randomly collected features of the plurality of clusters;

inputting the plurality of masks into the generator at a stage of synthesizing the red blood cell image; and synthesizing, by the generator, the plurality of masks into the red blood cell image.

11. The computer device according to claim 10, wherein the processor executes the computer program to achieve a complete network training target, and the complete network training target is as follows $$\min_G \left( \left( \max_{D_1, D_2} \sum_{k=1,2} L_{GAN}(G, D_k) \right) + \lambda_{FM} \sum_{k=1,2} L_{FM}(G, D_k) + \lambda_{PR} L_{PR}(G(x, E(x)), y) \right),$$

wherein, x represents the red blood cell shape data set, LGAN(G,Dk) represents an adversarial loss, and an expression of the adversarial loss is as follows:

$$E_{(x,y)}[\log D_k(x,y)] + E_x[\log(1 - D_k(x, G(x, E(x))))]$$

wherein, LFM(G,Dk) represents a feature matching loss, the feature matching loss is used to stabilize the training results and compensate visually generated results on a plurality of scales, and an expression of the feature matching loss is as follows:

$$E_{(x,y)} \sum_{i=1}^{T} \frac{1}{N_i} [\|D_k^{(i)}(x, y) - D_k^{(i)}(x, G(x, E(x)))\|_1],$$

wherein, $L_{PR}(G(x,E(X)),y)$ represents a perceptual reconstruction loss, and an expression of the perceptual reconstruction loss is as follows:

$$\sum_{i=1}^{N} \frac{1}{M_i} [\|F^{(i)}(y) - F^{(i)}(x, G(x, E(x)))\|_1].$$

12. The computer device according to claim 7, wherein after segmenting the red blood cell image background and the grayscale value of the 8-connected edge of the single pixel to obtain the binary image g(i,j), the processor executes the computer program to perform the following steps:

when the red blood cell image is segmented, for pixels in a red blood cell region, setting g(i,j)=1 and for the pixels in a background region, setting g(i,j)=0.

13. A non-transitory storage medium, wherein the non-transitory storage medium stores a computer instruction, and when the computer instruction runs on a computer, the computer is enabled to perform the following steps:

obtaining a plurality of clinical red blood cell images, dividing red blood cells of different shapes at different positions in each of the plurality of clinical red blood cell images into a plurality of submasks, and synthesizing the plurality of submasks corresponding to each of the plurality of clinical red blood cell images to generate one mask, and to obtain a plurality of masks corresponding to the plurality of red blood cell images, wherein each of the plurality of clinical red blood cell images comprises a plurality of red blood cells, and shapes and positions of the plurality of red blood cells on the same red blood cell image are identical or different;

collecting shape data of the plurality of red blood cells from the plurality of masks to obtain a training data set, calculating a segmentation boundary of each red blood cell in the training data set, and establishing a red blood cell shape data set based on the segmentation boundary of the each red blood cell, wherein the red blood cell shape data set is used to provide the shape data of the plurality of red blood cells during synthesis of a red blood cell image, wherein when the computer instruction runs on the computer, the computer is configured to collect the shape data of the plurality of red blood cells from the plurality of masks to obtain the training data set, to calculate the segmentation boundary of the each red blood cell in the training data set, and to establish the red blood cell shape data set based on the segmentation boundary of the each red blood cell, comprising the following steps:

identifying a discontinuous background region in a background image through image segmentation, marking the discontinuous background region, and determining a segmentation threshold;

performing an edge detection on cell membranes of the plurality of red blood cells in each red blood cell image region by using an edge detection method, and obtaining an 8-connected edge of a single pixel in the each red blood cell image region;

comparing the segmentation threshold with a grayscale value of a pixel, performing a pixel segmentation on the red blood cell image based on the segmentation threshold and obtaining a plurality of red blood cell image regions, and performing a grayscale stretching on the 8-connected edge of the single pixel in the each red blood cell image region to segment a red blood cell image background and a grayscale value of the 8-connected edge of the single pixel and obtaining a binary image;

performing a fill operation on the binary image to fill an interior of the each red blood cell in the binary image and obtaining a filled binary image; and performing a canny edge detection on the filled binary image and obtaining the segmentation boundary of the each red blood cell; wherein when the grayscale stretching is performed on the 8-connected edge of the single pixel in the each red blood cell image region, segmenting the red blood cell image background and the grayscale value of the 8-connected edge of the single pixel and obtaining the binary image g(i,j) by using a conversion formula of:

$$g(i, j) = \begin{cases} 1, f(i, j) \geq T \\ 0, f(i, j) < T \end{cases},$$

wherein, T represents the segmentation threshold, f(i,j) represents an input red blood cell image, and g(i,j) represents an output red blood cell image;
collecting distribution data of the each red blood cell in the red blood cell shape data set; and
synthesizing the red blood cell shape data set into a plurality of red blood cell images.

14. The non-transitory storage medium according to claim 13,
wherein when the computer instruction runs on the computer, the computer is enabled to synthesize the plurality of submasks corresponding to each of the plurality of clinical red blood cell images to generate one mask, and to obtain the plurality of masks corresponding to the plurality of red blood cell images, comprising the following steps:
invoking a red blood cell shape sampler to iteratively select a red blood cell shape $s_i$ from the red blood cell shape data set, wherein $1 \leq i \leq n$ and i is a positive integer, and $s_i$ represents red blood cells of different shapes at different positions; and
placing the selected red blood cell shape $s_i$ in the submasks to obtain the red blood cell shape and a position of the red blood cell in the red blood cell image, and using the obtained red blood cell shape and the position of the red blood cell in the red blood cell image as the mask; wherein
an expression of the mask is as follows:

$\{(s_1,l_1),(s_2,l_2), \ldots ,(s_n,l_n),\text{background}\}$ wherein, $s_1, s_2, \ldots,$ and $s_n$ all represent the shapes of the plurality of red blood cells, $l_n$ represents the positions of the plurality of red blood cells in the red blood cell image, $(s_n,l_n)$ represents a submask, n represents the total number of the plurality of red blood cells in the background red blood cell image, n is a positive integer, and represents a background pixel image of the red blood cell image.

15. The non-transitory storage medium according to claim 13, wherein when the computer instruction runs on the computer, the computer is configured to collect the distribution data of the each red blood cell in the red blood cell shape data set, comprising the following steps:
using an estimation of distribution algorithm to locate the position of the each red blood cell in the red blood cell shape data set and a position of each pixel in the each red blood cell;
based on a probability density function, the position of the each red blood cell and the position of the each pixel, calculating a prior probability that the each pixel is selected as a red blood cell center;
generating a possibility image set P(i) corresponding to the each red blood cell from the prior probability that the each pixel is selected as the red blood cell center and the each red blood cell;
sequentially selecting the prior probability from the possibility image set P(i) based on the value of i in ascending order, and simulating a real adhesion state of red blood cells for each value of i; and
calculating the distribution data of the each red blood cell in the red blood cell shape data set based on the position of the each red blood cell and the position of the each pixel in the real adhesion state of the plurality of red blood cells simulated for the each value of i.

16. The non-transitory storage medium according to claim 15, wherein when the computer instruction runs on the computer, the computer is configured to the red blood cell shape data set into the plurality of red blood cell images, comprising—the following steps:
inputting the red blood cell shape data set into a generator G;
converting, by the generator G, the segmentation mask in the red blood cell shape data set into the plurality of red blood cell images, and inputting the plurality of red blood cell images obtained through the conversion into two multi-scale discriminators D, wherein the plurality of red blood cell images obtained through the conversion are all images that simulate realistic red blood cells;
performing, by the two multi-scale discriminators D, discrimination at least once between a real red blood cell image and a synthesized red blood cell image within a preset period of time, and to train a neural network model;
outputting, by the two multi-scale discriminators D, training results;
combining, by a feature encoder network E, the training results with the red blood cell shape data set x to obtain a combined result, wherein the combined result is used to control a style of synthesizing the red blood cell image; the combined result is obtained by using a K-means clustering algorithm to generate a plurality of clusters from the training results and the red blood cell shape data set; the style of synthesizing the red blood cell image is determined by the feature encoder network E based on randomly collected features of the plurality of clusters;
inputting the plurality of masks into the generator at a stage of synthesizing the red blood cell image; and
synthesizing, by the generator, the plurality of masks into the red blood cell image.

17. The non-transitory storage medium according to claim 16, wherein when the computer instruction runs on the computer, the computer is enabled to execute a complete network training target, and the complete network training target is as follows:

$$\min_G \left( \left( \max_{D_1,D_2} \sum_{k=1,2} L_{GAN}(G, D_k) \right) + \lambda_{FM} \sum_{k=1,2} L_{FM}(G, D_k) + \lambda_{PR} L_{PR}(G(x, E(x)), y) \right),$$

wherein, x represents the red blood cell shape data set, $L_{GAN}(G,D_k)$ represents an adversarial loss, and an expression of the adversarial loss is as follows:

$E_{(x,y)}[\log D_k(x,y)] + E_x[\log(1-D_k(x,G(x,E(x))))]$ wherein, $L_{FM}(G,D_k)$ represents a feature matching loss, the feature matching loss is used to stabilize the training results and compensate visually generated results on a plurality of scales, and an expression of the feature matching loss is as follows:

$$E_{(x,y)}\sum_{i=1}^{T}\frac{1}{N_i}[\|D_k^{(i)}(x,y)-D_k^{(i)}(x,G(x,E(x))\|1],$$

wherein, $L_{PR}(G(x,E(x)),y)$ represents a perceptual reconstruction loss, and an expression of the perceptual reconstruction loss is as follows:

$$\sum_{i=1}^{N}\frac{1}{M_i}[\|F^{(i)}(y)-F^{(i)}(x,G(x,E(x)))\|1].$$

\* \* \* \* \*